United States Patent [19]

Mayer

[11] 4,096,197

[45] Jun. 20, 1978

[54] PROCESS FOR REGENERATING FLUOROSULFURIC ACID CATALYST

[75] Inventor: Ivan Mayer, Summit, N.J.

[73] Assignee: Exxon Research & Engineering Co., Linden, N.J.

[21] Appl. No.: 772,641

[22] Filed: Feb. 28, 1977

[51] Int. Cl.$^2$ .............................................. C07C 3/54
[52] U.S. Cl. .......................... 260/683.47; 260/683.58; 252/411 R
[58] Field of Search ...................... 260/683.47, 683.58, 260/683.48, 683.62

[56] References Cited

U.S. PATENT DOCUMENTS

| Re. 29,084 | 12/1976 | Anderson et al. | 260/683.48 |
| 3,349,146 | 10/1947 | Witt | 260/683.62 |
| 3,766,293 | 10/1973 | Parker et al. | 260/683.62 |
| 3,887,635 | 6/1975 | Parker et al. | 260/683.47 |

Primary Examiner—George Crasanakis
Attorney, Agent, or Firm—John W. Ditsler

[57] ABSTRACT

An improved process for regenerating an alkylation catalyst comprising fluorosulfuric acid, said catalyst being at least partially deactivated, which comprises the method of:

(1) removing a portion of the fluorosulfuric acid from said catalyst by contacting same with a paraffin to form a liquid acid phase containing fluorosulfuric acid and an organic sludge formed during said alkylation and a gas phase containing said paraffin and fluorosulfuric acid;

(2) contacting the liquid acid phase formed in step (1) with water to form an acid-water mixture, thereby converting at least a portion of the fluorosulfuric acid contained therein to hydrogen fluoride and sulfuric acid;

(3) removing at least a portion of the hydrogen fluoride from said acid-water mixture formed in step (2) by contacting same with a paraffin to form a gaseous phase containing hydrogen fluoride and paraffin; and (4) treating the gas phases formed in steps (1) and (3) with sulfur trioxide to regenerate the fluorosulfuric acid.

In a preferred embodiment, at least a portion of the regenerated fluorosulfuric acid is recycled to the alkylation zone for use as an alkylation catalyst therein.

17 Claims, 1 Drawing Figure

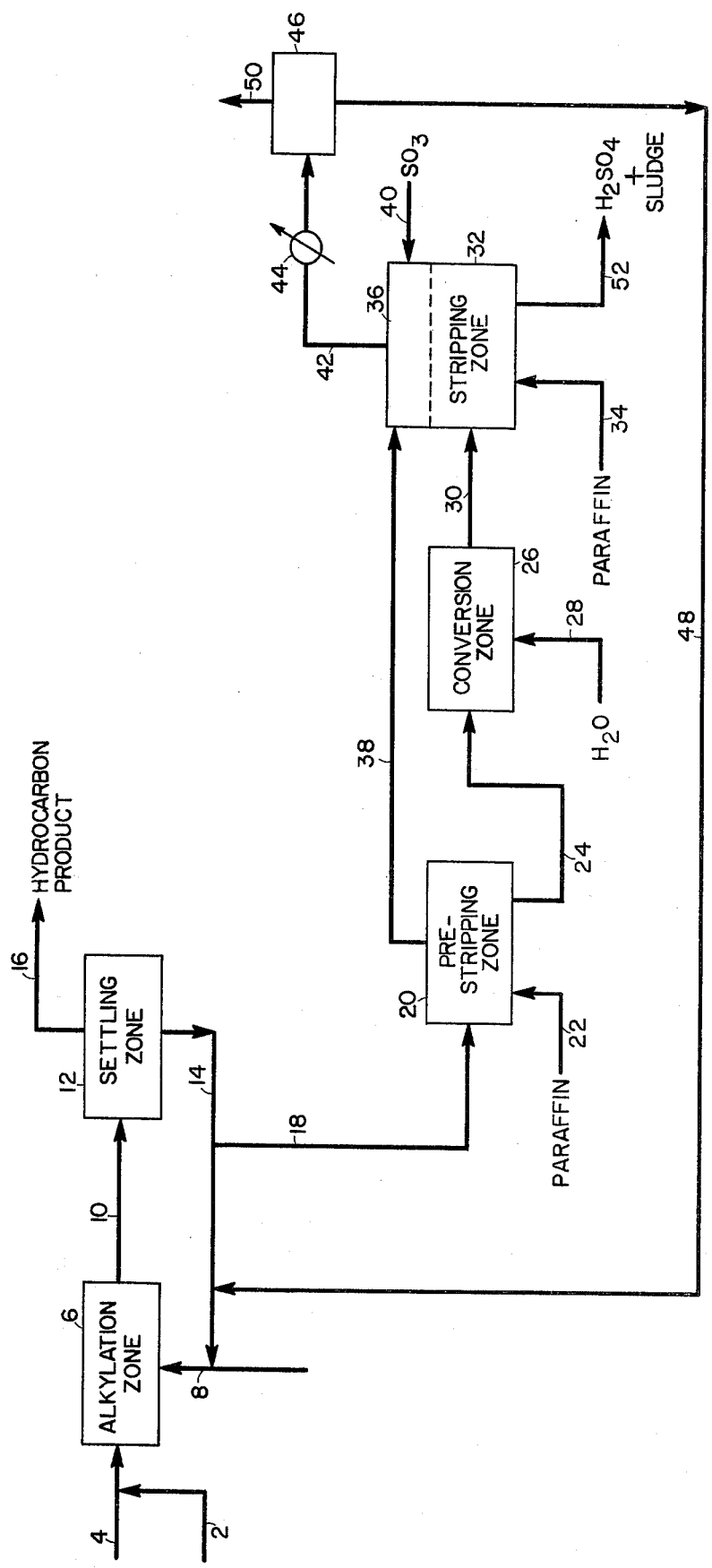

PROCESS FOR REGENERATING FLUOROSULFURIC ACID CATALYST

BACKGROUND OF THE INVENTION

1. Field of the Invention

The present invention relates to a process for regenerating a catalyst of the type used in hydrocarbon conversion processes. More particularly, this invention relates to a process for regenerating a catalyst comprising fluorosulfuric acid, at least a portion of said catalyst having become deactivated due to the formation of stable catalytically inert species during contact with a hydrocarbon feedstock in an alkylation process.

2. Description of the Prior Art

It is well known in the prior art that as the alkylation reaction proceeds, an organic material will form and will accumulate in the fluorosulfuric acid catalyst phase. The material has been given a variety of names including red oil, sludge, organic sludge, acid oil and the like. This organic material is a natural by-product of acid-catalyzed hydrocarbon reactions such as occur during alkylation and has been described in the literature as a conjunct polymer (see Miron, S. and Lee, R. J., "Molecular Structure of Conjugated Polymers," J. Chem. Eng. Data, Vol. 8, p. 150–160 (1963), the disclosures of which are incorporated herein by reference). These conjunct polymers are complex mixtures of olefinic, conjugated cyclic hydrocarbons that may be formed from any type of hydrocarbon except aromatics. More specifically, they are believed to be cyclic polyolefinic hydrocarbons with a high proportion of conjugated double bonds, no two of which are in the same ring. Five membered ring systems predominate, but larger, and possibly also smaller, rings are believed to be present. The accumulation of this material will ultimately cause the activity of fluorosulfuric acid catalysts to decline until said catalysts cease to exhibit economic activity. In such cases, depending upon economic factors, the catalyst may be replaced or regenerated to restore desired activity levels.

One method for regenerating catalysts comprising fluorosulfuric acid has been suggested in U.S. Pat. No. 3,766,293, the disclosures of which are incorporated herein by reference. According to this metal, an alkylation catalyst comprising fluorosulfuric acid, at least a portion of which has become deactivated, may be regenerated by (1) contacting said catalyst with water so as to convert at least a portion of the fluorosulfuric acid to hydrogen fluoride and sulfuric acid; (2) removing at least a portion of the hydrogen fluoride from said catalyst by contacting the same with a paraffin so as to form a hydrocarbon phase containing hydrogen fluoride; and (3) treating said hydrocarbon phase with sulfur trioxide to regenerate the fluorosulfuric acid. However, since sulfur trioxide is a fairly expensive reagent, it would be desirable to have available a simple and convenient method for minimizing the consumption of sulfur trioxide in step (3) of U.S. Pat. No. 3,766,293.

SUMMARY OF THE INVENTION

Now according to the present invention, an improved process for regenerating an alkylation catalyst comprising fluorosulfuric acid has been discovered, said process comprising:

(1) removing a portion of the fluorosulfuric acid from said catalyst by contacting same with a paraffin to form a liquid acid phase containing fluorosulfuric acid and an organic sludge formed during said alkylation and a gas phase containing said paraffin and fluorosulfuric acid;

(2) contacting the liquid acid phase formed in step (1) with water to form an acid-water mixture, thereby converting at least a portion of the fluorosulfuric acid contained in said liquid acid phase to hydrogen fluoride and sulfuric acid;

(3) removing at least a portion of the hydrogen fluoride from said acid-water mixture of step (2) by contacting same with a paraffin so as to form a gas phase containing paraffin and hydrogen fluoride; and (4) treating the gas phases from steps (1) and (3) with sulfur trioxide so as to regenerate the fluorosulfuric acid.

Use of the present invention permits recovery of a portion of the fluorosulfuric acid present in the deactivated or partially deactivated catalyst prior to undergoing the reaction with water in step (2) above. This results in a reduced consumption of sulfur trioxide since, as will be discussed hereinbelow, one mole of sulfur trioxide is conserved for each mole of fluorosulfuric acid that is not reacted in step (2). This results in a significant reduction in regeneration costs because sulfur trioxide is fairly expensive. In a preferred embodiment, at least a portion of the regenerated fluorosulfuric acid is recycled to the alkylation process.

BRIEF DESCRIPTION OF THE DRAWING

The single FIGURE is a flow diagram illustrating one embodiment of the present invention.

DETAILED DESCRIPTION OF THE INVENTION

Having thus described the invention in general terms, reference is now made to the FIGURE which shows an alkylation process using a catalyst system such as that described in U.S. Pat. No. 3,887,635, the disclosures of which are incorporated herein by reference. Such details are included as are necessary for a clear understanding of how the present invention may be applied in the regeneration of an alkylation catalyst comprising fluorosulfuric acid, said catalyst being at least partially deactivated. No intention is made to unduly limit the scope of the present invention to the particular configuration shown as variations obvious to those having ordinary skill in the art of alkylation and other unit operation processes are included within the broad scope of the present invention.

Referring now to the FIGURE, there is shown an olefin stream in line 2 which is, preferably, admixed with a paraffin stream in line 4 before introducing the combined stream into alkylation zone 6. If desired, however, the olefin and paraffin streams can be fed directly into alkylation zone 6. The olefin concentration in the feed ranges from 0.5 to 25 volume percent based on total feed and preferably below 10 volume percent. Translated into volume ratios, high volume ratios of paraffin to olefin ranging from 10:1 to 200:1 or higher are preferred, although somewhat lower ratios may be used, e.g., 3:1. Correspondingly high volume ratios of paraffin to olefin are also desired within the alkylation zone. Preferably, the parafin/olefin ratio therein ranges from about 5:1 to 2,000:1 or higher.

Suitable olefinic reactants include $C_2$-$C_{12}$ terminal and internal monoolefins such as ethylene, propylene, isobutylene, butene-1, butene-2, the pentenes (e.g., trimethylethylene) and similar higher monoolefinic hydrocarbons of either a straight chain or a branched chain structure. Preferably, the $C_2$–$C_6$ monoolefins are used, although the highly-branched $C_7$–$C_{12}$ monoolefins may also be used. The reaction mixtures may also contain small amounts of diolefins and other type hydrocarbons normally present in refinery hydrocarbon streams. Although it is desirable from an economic standpoint to use the normally gaseous olefins as reactants, normally liquid olefins may be used. Thus, reactable polymers, copolymers, interpolymers, cross-polymers, and the like, of the above-mentioned olefins, such as, for example, the diisobutylene and triisobutylene polymers, the codimer of normal butylene and isobutylene of butadiene and isobutylene, may be employed as an olefinic reactant. Mixtures of two or more of the olefins described above can be used as the process feedstock.

$C_2$, $C_3$, $C_4$ and/or $C_5$ olefin cuts from thermal and/or catalytic cracking units; field butanes which have been subjected to prior isomerization and/or partial dehydrogenation treatment; refinery stabilizer bottoms; spent gases; normally liquid products from sulfuric acid or phosphoric acid catalyzed polymerization and copolymerization processes; and products, normally liquid in character, from thermal and/or catalytic cracking units, are all excellent feedstocks for the present alkylation process. Such feeds are preferably dried to control excess water buildup, i.e., about 5 to 15 wppm or less of water, before entering the alkylation zone.

The paraffinic feedstocks that can be reacted with the olefins desirably comprise straight and/or branched chain $C_4$–$C_{10}$ paraffins such as hexane, butane and the like, and preferably $C_4$–$C_6$ isoparaffins such as isobutane, isopentane, isohexane and the like. While open chain hydrocarbons are preferred, cycloparaffins such as methylcyclopentane may also be used.

Returning to the FIGURE, a catalyst comprising fluorosulfuric acid and one or more moderators is shown being introduced into alkylation zone 6 via line 8. Generally, the moderator contains at least one oxygen atom per molecule and includes water, aliphatic and cycloaliphatic alcohols and ethers, aliphatic, cycloaliphatic and aromatic sulfonic and carboxylic acids and their derivatives, inorganic acids and other oxygen-containing organic compounds. By the term "moderator" is meant a compound which, in combination with fluorosulfuric acid, produces a catalyst system of reduced acidity vis-a-vis the fluorosulfuric acid, and thereby decreases the probability of undesirable competing side reactions which have a detrimental effect on product quality, while increasing catalyst selectivity to desirable highly branched paraffinic products, thus resulting in high quality alkylate product. Various moderators that can be employed in the present catalyst system are shown at column 2, lines 38–67, column 3, lines 16–68 and column 4, lines 1–23 of U.S. Pat. No. 3,887,635.

Preferred catalyst moderators contain either a hydroxy group such as alcohols or a hydroxy group precursor, such as ethers, which, it is speculated, can potentially cleave to form alcohols under the acidic conditions of the subject invention. Of these, the more preferred moderators are the alcohols and water, the most preferred being water. It is noted that the catalyst moderator and the fluorosulfuric acid can be premixed prior to introduction into the reactor, thereby forming the catalyst system. The catalyst may also be formed in situ.

The exact mechanism by which the moderator compounds effectuate increased catalyst selectivity while reducing competitive side reactions is not known. However, the active catalyst species employed herein are postulated to be an equilibrium mixture comprising several components. By way of illustration, it is speculated that the addition of water to fluorosulfuric acid results in initial dissociation of the strong acid followed by hydrolysis:

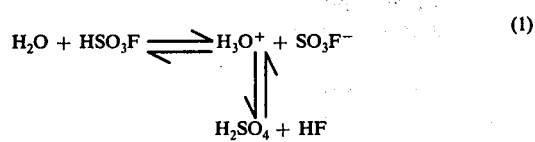

The equilibrium is believed to lie towards the right and, therefore, little, if any, free water should exist in the strong acid system. Similar mechanisms can be postulated for other moderators such as alcohols and ethers.

By the very nature of the postulated mechanism, it is clear that the manner in which the active catalytic system is formed is immaterial. Thus, in the above illustration mixing HF and $H_2SO_4$ in equal molar amounts should result in the same catalyst system as would be obtained by mixing water with $HSO_3F$. The active catalyst system may also be formed by mixing HF, $H_2SO_4$ and $HSO_3F$ in appropriate amounts. Hence, when the catalyst system is described as "being formed from" a strong acid and a moderator, it is not meant to be limited to any one catalyst formation mode; rather, this description is used merely for convenience in providing a simple definition of the active catalyst system.

The amount of moderator used in forming the catalyst system is an important variable in the production of high quality alkylate. The desired amounts of moderator will vary dependent, in part, on the alkylation temperature. Thus, for example, at temperatures between about 0° to 40° F, useful amounts of moderator can range between about 5 and 45 mole % based on acid. In some instances, however, it may be desirble to use somewhat lower or higher amount of moderator, e.g., 50 mole % based on acid, where, for example, different catalyst activity or selectivity is desired.

At high alkylation temperatures, e.g., between about 40° and 100° F, increased amount of moderator may be desirable due to the increased strong acid activity. Thus, an amount of moderator ranging between about 50 and 100 mole % based on acid may be used at these higher temperatures. In fact, under appropriate conditions, these higher amounts of moderator may also be utilized at the lower temperatures disclosed hereinabove, if desired. A preferred catalyst is one formed from fluorosulfuric acid and from about 5 to 100 mole %, based on acid, of (1) water, (2) a $C_1$–$C_7$ saturated aliphatic monohydroxyalcohol, or (3) a mixture of water and said alcohol.

Although the broad concentration ranges are generally independent of the type moderator used, the preferred or optimal range will vary depending on the structure of the moderator, the reaction temperature, the concentration and nature of the olefin in the feed, the amount of organic sludge present, the olefin space velocity and the like.

In addition to being used in classical alkylation processes as hereinabove described, the catalyst system employed herein may also be used in self-alkylation processes. The $C_4$–$C_{16}$ branched chain olefins and $C_4$–$C_8$ isoparaffins are preferred reactants. The process is generally conducted in the liquid phase whereby the isoparaffin is dimerized and the olefin is sacrificed by being saturated, thus producing an alkylate-type product of high quality. Self-alkylation processes are generally described in U.S. Pat. No. 3,150,204. Undesired side reactions are minimized using these catalyst systems, thereby providing high yields of the desired products.

In general, the amount of olefin contacted with the catalyst can range from about 0.05 to 1000 volumes of olefin per hour per volume of catalyst inventory in the reactor (V/V/Hr.), i.e., olefin space velocity. Preferably, the olefin space velocity ranges from about 0.05 to 10.0 V/V/Hr., and still more preferably from about 0.05 to 1.0 V/V/Hr., e.g., 0.1 V/V/Hr. The volume % of total catalyst in the reaction mixture or emulsion (when liquid phase operations are used) in the alkylation zone can range from about 30 to 80 volume % based on total reaction mixture and preferably from about 50 to 70 volume %. The isoparaffin concentration, including alkylate, in the hydrocarbon phase (in a liquid phase process) can range from 40 to about 100 volume % based on the total volume of the hydrocarbon phase and preferably from 50 to 90 volume %. Such isoparaffin concentrations can be maintained by recycling unreacted isoparaffin to the alkylation zone.

The process may be carried out either as a batch or continuous type of operation, although it is preferred for economic reasons to carry out the process continuously. It has been generally established that in alkylation processes, the more intimate the contact between the feedstock and the catalyst the better the yield of saturated product obtained. With this in mind, the present process, when operated in either a batch or in a continuous manner, is characterized by the use of vigorous mechanical stirring or mixing of the reactants with the catalyst.

In continuous operations, as that of the embodiment shown in the drawing, the reactants may be maintained at sufficient pressures and temperatures to maintain them substantially in the liquid state and then continuously forced through dispersion devices into the alkylation zone. The dispersion devices may be jets, porous thimbles and the like. The reactants are subsequently mixed with the catalyst in alkylation zone 6 by conventional mixing means (not shown) such as mechanical agitators and the like. While the alkylation reaction can be carried out at a temperature within the range of from about −80° to +100° F, fairly low reaction temperatures, preferably within the range of from about −80° to +70° F, and most preferably within the range of from about −20° to about +40° F, are usually employed. Where the reaction is carried out at temperatures about +10° F, or higher, it is necessary that the reaction be conducted under superatmospheric pressure, if the reactants and/or the catalysts are to be maintained substantially in a liquid state. Typically, the alkylation reaction is conducted at pressures varying from about atmospheric to about 300 psia.

In general it is preferably to employ pressures sufficiently high to maintain the reactants in the liquid phase although a vapor phase operation is also contemplated. Autorefrigerated reactors and the like may be employed to maintain liquid phase operation. Although it is preferred to run the reaction neat, solvents or diluents may be employed if desired.

After allowing sufficient residence time for the reaction to progress, typically on the order from about one minute to one hour or more, the reaction mixture which contains hydrocarbon and deactivated or partially deactivated catalyst (often referred to as the "emulsion mixture") is withdrawn from the alkylation zone 6 via line 10 and passed into a settling zone 12. The reaction mixture will separate in zone 12 into a heavy acid phase containing the fluorosulfuric acid, sulfuric acid, hydrogen fluoride and moderator (assumed to be water for the purpose of illustration in the following discussion), as well as organic sludge formed during said alkylation process, and a hydrocarbon phase containing the alkylate product along with smaller amounts of fluorosulfuric acid, hydrogen fluoride and water which are dispersed and/or dissolved in said alkylate product. The acid phase is withdrawn from settling zone 12 via line 14 and at least a portion thereof can be recycled to alkylation zone 6 via line 8 or charged to another alkylation zone, if desired. The hydrocarbon phase is withdrawn from settling zone 12 via line 16.

As shown in the FIGURE, a purge stream 18 of the heavy acid phase is withdrawn from line 14 and passed into the prestripping zone 20 and intimately contacted with a vaporized paraffin introduced via line 22. Preferred paraffins are $C_3$–$C_6$ paraffins, more preferably $C_4$ paraffins. Normal butane is the preferred paraffin. As a result of said contacting, a portion, preferably a major portion, more preferably from about 60 to 90%, of both the hydrofluoric acid and the fluorosulfuric acid is stripped from said purge stream, thereby forming a gas phase containing paraffin, fluorosulfuric acid and hydrogen fluoride and a liquid phase containing fluorosulfuric acid, organic sludge and sulfuric acid and traces of hydrogen fluoride. The amount of stripping agent employed is that required to remove the desired amount of fluorosulfuric acid. It should be pointed out that hydrofluoric acid and sulfuric acid are present in streams 14 and 18 because the fluorosulfuric acid is partially dissociated when contacted with the moderator, e.g., water. If no moderator is employed, small amounts of water are normally introduced into the alkylation zone (e.g., with the feed) such that said partial dissociation will occur. Be that as it may, however, the present regeneration process is also applicable to a fluorosulfuric acid catalyst that has not been hydrolyzed.

The liquid phase then passes from pre-stripping zone 20 via line 24 to conversion zone 26 wherein it is contacted with water injected via line 28 in an amount sufficient to convert the fluorosulfuric acid to free hydrogen fluoride and sulfuric acid according to the reaction:

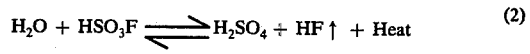

$$H_2O + HSO_3F \rightleftharpoons H_2SO_4 + HF \uparrow + \text{Heat} \qquad (2)$$

In one embodiment of the invention, it may be desirable to add up to a mole of water in excess of the stoichiometric amount required. Preferably, less than about 0.5 mole excess water is used. The resulting stream of water, hydrogen fluoride, sulfuric acid and organic sludge is then passed from conversion zone 26 via line 30 into stripping zone 32 and intimately contacted therein with a paraffin introduced via line 34, thereby stripping at least a portion, preferably a major portion, more preferably substantially all (i.e., about 95% or more) of the hydrogen fluoride from said stream. The gas phase from pre-stripping zone 20 is introduced into the upper section 36 of stripping zone 32 via line 38 wherein the hydrogen fluoride present therein, as well as that removed in the lower section of stripping zone 32, is reacted with at least a stoichiometric amount of sulfur trioxide, based on HF, so that at least a portion, preferably substantially all, of the hydrogen fluoride present is converted to fluorosulfuric acid according to the reaction:

$$HF + SO_3 \rightarrow HSO_3F + Heat \qquad (3)$$

The sulfur trioxide, which is introduced via line 40, thus regenerates the fluorosulfuric acid catalyst which, together with the paraffin and perhaps a trace of water is taken overhead via line 42, condensed in condensation zone 44, and passed to separation zone 46 wherein the fluorosulfuric acid is separated from the paraffin present in the stream. The regenerated fluorosulfuric acid stream, which may contain negligible amounts of water (typically less than 100 wppm since most all of the water present will react with sulfur trioxide to form sulfuric acid), is withdrawn from the separation zone via line 48 and at least a portion thereof may be combined with the recycle stream 14 for return to alkylation zone 6 via line 8. The paraffin stream is removed from separation zone 46 via line 50. If desired, at least a portion of the paraffin stream may be recycled to conversion zones 26 and 36 for temperature control purposes or may be used as part of the stripping agent in zone 20. Additional hydrocarbon stripping agent can be introduced into said stripping zones if desired. Sulfuric acid and the sludge formed during the alkylation process can be removed from the bottom of stripping zone 32 via line 52 and sent to sulfuric acid regeneration (not shown) for sludge removal and reconcentration, or it can be discharged. Alternatively, the sulfuric acid-sludge stream can be employed for removing dissolved and/or dispersed fluorosulfuric acid from a hydrocarbon phage 16.

The particular temperature and pressure employed in the conversion and stripping zones are, in general, determined by economic factors such as cost or availability of stripping agent, cost of $SO_3$, etc. Normally, zone 20 should be operated at a temperature above that at which the vapor pressure of fluorosulfuric acid becomes sufficiently low such that uneconomical amounts of stripping agent are required. It is also desirable to operate zone 20 at as high a temperature as possible because better stripping is obtained and less stripping agent is required. However, as disclosed in application Ser. No. 772,636 filed on the same date herewith, undesirable side reactions between the fluorosulfuric acid and acidic components in the catalyst (e.g., HF, $H_2SO_4$ and the like) and the hydrocarbon stripping agent become excessive at elevated temperatures, i.e., temperatures above about 250° F. Such reactions result in the formation of a polymer-like material, e.g., coke, that could "plug" the system. Thus, while elevated temperatures would normally be preferred, it has been found necessary, as disclosed in Ser. No. 772,636, to avoid contacting the acid components with the hydrocarbon stripping agent at temperatures in excess of 250° F. Therefore, as disclosed in Ser. No. 772,636, it is desirable that the temperature of the conversion and stripping zones be maintained below 250° F and in the range of from about 120° to about 250° F, preferably in the range of from about 130° to about 210° F, and more preferably in the range of from about 140° to 170° F. Total pressure of the zones can also vary according to the economic factors mentioned above. In general, however, the total pressure will range from about atmospheric pressure to about 170 psia, preferably about 120 psia and more preferably from about 20 to about 90 psia.

Stripping of the deactivated or partially deactivated catalyst with a paraffin in zone 20 prior to contact with water in zone 26 results in reduced consumption of sulfur trioxide since for each mole of fluorosulfuric acid that does not undergo reactions (2) and (3) above, one mole of sulfur trioxide is conserved. In addition, the sulfuric acid produced via reaction (2) is reduced by a corresponding amount, such that less sulfuric acid will be processed in the sulfuric acid regeneration process. Thus, when a deactivated or partially deactivated catalyst comprising fluorosulfuric acid is regenerated according to the present invention, both the sulfuric acid produced and the sulfur trioxide required are reduced by from about 35 to 90%, i.e., the amount of fluorosulfuric acid recovered ranges from about 35 to about 90% of that present in purge stream 18. This represents a significant cost reduction for regenerating fluorosulfuric acid. The lower level of recovery represents that expected using about one theoretical stripping tray and a molar ratio of stripping agent to catalyst plus sludge of about 7.5/1. The higher recovery represents that expected using about two theoretical stripping trays and a molar ratio of stripping agent to catalyst plus sludge of about 14/1. The specific amount of fluorosulfuric acid removed during pre-stripping is a function of economics incuding, for example, the lower overall consumption of sulfur trioxide versus the costs associated with paraffin stripping plus the conversion and recovery described in reactions (2) and (3).

As previously noted, hydrocarbon phase 16 contains dissolved and/or dispersed fluorosulfuric acid, water, hydrogen fluoride from partial dissociation of the acid, and other acidic materials such as sulfur dioxide, etc. If desired, the acid materials which are dissolved and/or dispersed in hydrocarbon phase 16 can be effectively removed by scrubbing said hydrocarbon phase with sulfuric acid. The sulfuric acid is preferably concentrated, being 98.0 to 100% $H_2SO_4$ as limited by the freezing point of the acid, but somewhat more dilute acid (95–97.9%) can also be used without substantial detriment to the efficiency of the process. The manner of scrubbing may be by any conventional means, such as by passing the sulfuric acid and hydrocarbons through a mixing orifice, a countercurrent contacting tower or by injecting them into a centrifugal pump, etc., as long as intimate contact between the hydrocarbon phase and the sulfuric acid is attacined. However, countercurrent-staged operations are preferred. The ratio of acid to hydrocarbon is not critical, but can vary from about 5 to 95% of the hydrocarbon stream. The temperature for scrubbing generally ranges from about 20° to 100° F, but must be above the freezing point of sulfuric acid. The pressure may be any pressure from atmospheric to about 500 psig. The resulting phases are settled after contacting. The hydrocarbon phase containing alkylate product may undergo further treatment to remove trace amounts of any acid materials present therein. Fluorosulfuric acid present in the sulfuric acid phase thus settled may be removed therefrom by introducing the acid phase into the regeneration process described above, e.g., into pre-stripping zone 20, or, preferably, directly into conversion zone 26.

The stripping zones and conversion tower are conventional equipment suitable for gas-liquid or liquid-liquid contacting and are available from various equipment vendors. As such, they do not form a part of this invention. However, Hastelloy B or C is normally employed although at lower temperatures with substantially no free water present, carbon steel may be used. The conversion and stripping zones may comprise one vessel if desired.

It should be pointed out that the level of activity at which the fluorosulfuric acid catalyst should be regenerated is not only a matter of ability to catalyze the alkylation reaction, but also a matter of economics. For example, it may be desirable to regenerate a mildly deactivated catalyst to essentially fresh catalyst activity rather than allow the catalyst to be reduced to a much lower level of activity and be regenerated to fresh or to less than fresh activity. Thus, as used herein, the term "regeneration" or "regenerated" means recovering a fluorosulfuric acid catalyst that possesses a greater activity for alkylation than that possessed by the deactivated or partially deactivated catalyst. It should be understood that the regeneration process of the present invention is applicable to catalysts such as those defined above which have lost some degree of activity and that the regeneration may only partially restore the lost activity.

Although the present regeneration process has been discussed with reference to the alkylation process described in U.S. Pat. No. 3,887,635, it should be understood that it is applicable to any alkylation process that employs fluorosulfuric acid (see, for example, U.S. Pat. Nos. 3,922,319 and 3,928,487, the disclosures of which are incorporated herein by reference), including those processes that form fluorosulfuric acid from a strong acid and a moderator, e.g., mixing sulfuric acid and hydrofluoric acid in appropiate amounts, alone or in the presence of $HSO_3F$. (See, for example, U.S. Pat. No. 3,956,418.)

What is claimed is:

1. In an alkylation process which comprises:
   (a) contacting an olefin with a paraffin in an alkylation zone under alkylation conditions and with a catalyst comprising fluorosulfuric acid which includes a moderator in an amount of 5 to 100 mole %, based on acid, of (1) water, (2) a $C_1$–$C_7$ saturated aliphatic monohydroxy alcohol, or (3) a mixture of water and said alcohol to form a reaction mixture of an acid catalyst phase containing fluorosulfuric acid, hydrogen fluoride, sulfuric acid and an organic sludge formed during said process and a hydrocarbon phase containing alkylate product;
   (b) separating said hydrocarbon phase containing alkylate product from said acid catalyst phase, the improvement which comprises regenerating said acid catalyst phase according to the following steps:
   (c) stripping a portion of the fluorosulfuric acid from the acid catalyst phase separated in step (b) with a paraffin to form a stripped acid phase containing fluorosulfuric acid, sulfuric acid and said organic sludge and a gaseous phase containing paraffin, fluorosulfuric acid and hydrogen fluoride;
   (d) contacting said stripped acid phase formed in step (c) with water to form an acid-water mixture, thereby converting at least a portion of the fluorosurfuric acid contained therein to hydrogen fluoride and sulfuric acid;
   (e) stripping at least a portion of the hydrogen fluoride from said acid-water mixture formed in step (d) with a paraffin to form a gaseous phase comprising hydrogen fluoride and paraffin and a liquid phase comprising sulfuric acid and organic sludge;
   (f) treating the gaseous phases formed in step (c) and step (e) with sulfur trioxide to convert the hydrogen fluoride present therein into fluorosulfuric acid.

2. The process of claim 1 wherein the fluorosulfuric acid of step (e) is recycled to said alkylation zone in step (a).

3. The process of claim 1 wherein said moderator is water.

4. The process of claim 1 wherein the paraffin used for stripping is a $C_4$ paraffin.

5. The process of claim 4 wherein the $C_4$ paraffin is n-butane.

6. The process of claim 1 wherein a major portion of the fluorosulfuric acid is stripped from the acid catalyst phase in step (c).

7. The process of claim 1 wherein the contacting of step (a) is carried out at a temperature within the range of from about −80° to about +100° F. and the stripping of step (c) and step (e) is carried out at a temperature within the range of from about 120° to about 250° F.

8. The process of claim 1 wherein the acid catalyst phase of step (b) contains HF.

9. The process of claim 1 wherein from about 60 to about 90% of the fluorosulfuric acid is stripped from the acid catalyst phase in step (c).

10. In an alkylation process which comprises:
    (a) contacting an olefin with a paraffin in an alkylation zone under alkylation conditions and with a catalyst comprising fluorosulfuric acid which includes a moderator in an amount of from about 5 to 100 mole %, based on acid, of (1) water, (2) a $C_1$–$C_7$ saturated aliphatic monohydroxy alcohol or (3) a mixture of water and said alcohol to form a reaction mixture of an acid catalyst phase containing fluorosulfuric acid, hydrogen fluoride, sulfuric acid and an organic sludge formed during said process and a hydrocarbon phase containing alkylate product;
    (b) separating said hydrocarbon phase containing alkylate product from said acid catalyst phase, said hydrocarbon phase containing a portion of the fluorosulfuric acid;
    (c) washing said hydrocarbon phase with an acid comprising sulfuric acid thereby removing at least a portion of the fluorosulfuric acid from said hydrocarbon phase and separating a sulfuric acid phase containing said fluorosulfuric acid from said hydrocarbon phase containing the alkylate product, the improvement which comprises regenerating said acid catalyst phase according to the following steps:
    (d) stripping a portion of the fluorosulfuric acid from the acid catalyst phase separated in step (b) with a paraffin to form a stripped acid phase containing fluorosulfuric acid, sulfuric acid and said organic sludge and a gaseous phase containing said paraffin, fluorosulfuric acid and hydrogen fluoride:
    (e) contacting said stripped acid phase formed in step (d) and the sulfuric acid phase separated in step (c) with water to form an acid-water mixture, thereby converting at least a portion of the fluorosulfuric acid contained therein to hydrogen fluoride and sulfuric acid;
    (f) stripping at least a portion of the hydrogen fluoride from said acid-water mixture formed in step (e)

with a paraffin to form a gaseous phase comprising hydrogen fluoride and paraffin and a liquid phase comprising sulfuric acid and organic sludge;

(g) treating the gaseous phases formed in step (d) and step (f) with sulfur trioxide to convert the hydrogen fluoride present therein to fluorosulfuric acid.

11. The process of claim 10 wherein the fluorosulfuric acid of step (g) is recycled to said alkylation zone in step (a).

12. The process of claim 10 wherein said moderator is water.

13. The process of claim 10 wherein a major portion of the fluorosulfuric acid is stripped from the acid catalyst phase in step (d).

14. The process of claim 10 wherein the contacting of step (a) is carried out at a temperature within the range of from about −80° to about −100° F. and the stripping of step (d) and step (f) is carried out at a temperature within the range of from about 120° to about 250° F.

15. The process of claim 10 wherein the acid catalyst phase of step (b) contains HF.

16. The process of claim 10 wherein the paraffin used for stripping is a $C_4$ paraffin.

17. The process of claim 10 wherein the liquid phase comprising sulfuric acid and organic sludge of step (f) is employed to wash the hydrocarbon phase in step (c).

* * * * *